United States Patent
Hérambert et al.

(10) Patent No.: US 12,383,650 B2
(45) Date of Patent: Aug. 12, 2025

(54) USE IN AN ELECTRIC PERFUME DIFFUSER OF AN AQUEOUS PERFUME COMPOSITION CONTAINING A SURFACTANT AND A PRESERVATIVE

(71) Applicant: PRODUITS BERGER, Grand Bourgtheroulde (FR)

(72) Inventors: Céline Hérambert, La Londe (FR); Corinne Gerard, Incarville (FR)

(73) Assignee: PRODUITS BERGER, Grand Bourgtheroulde (FR)

( * ) Notice: Subject to any disclaimer, the term of this patent is extended or adjusted under 35 U.S.C. 154(b) by 710 days.

(21) Appl. No.: 17/628,503

(22) PCT Filed: Jun. 30, 2020

(86) PCT No.: PCT/FR2020/051137
§ 371 (c)(1),
(2) Date: Jan. 19, 2022

(87) PCT Pub. No.: WO2021/014063
PCT Pub. Date: Jan. 28, 2021

(65) Prior Publication Data
US 2022/0280672 A1    Sep. 8, 2022

(30) Foreign Application Priority Data
Jul. 22, 2019 (FR) .................................. 1908306

(51) Int. Cl.
*A61L 9/01*    (2006.01)
*C11B 9/00*    (2006.01)

(52) U.S. Cl.
CPC .................... *A61L 9/01* (2013.01); *C11B 9/00* (2013.01); *A61L 2209/132* (2013.01)

(58) Field of Classification Search
None
See application file for complete search history.

(56) References Cited

U.S. PATENT DOCUMENTS

| | | | |
|---|---|---|---|
| 2014/0093471 A1* | 4/2014 | Porter | A61L 9/01 424/76.1 |
| 2016/0024426 A1* | 1/2016 | Sivik | C11D 1/62 510/516 |

FOREIGN PATENT DOCUMENTS

| | | | |
|---|---|---|---|
| CN | 105477670 A | * | 4/2016 |
| EP | 2158895 A2 | | 3/2010 |
| WO | 2021014063 A1 | | 1/2021 |

OTHER PUBLICATIONS

Foreign Communication from a Related Counterpart Application, International Search Report dated Oct. 20, 2020, International Application No. PCT/FR2020/051137 filed on Jun. 30, 2020.
Foreign Communication from a Related Counterpart Application, Written Opinion dated Oct. 20, 2020, International Application No. PCT/FR2020/051137 filed on Jun. 30, 2020.

* cited by examiner

*Primary Examiner* — Nannette Holloman
(74) *Attorney, Agent, or Firm* — Conley Rose, P.C.

(57) ABSTRACT

The present invention relates to the use of a scented aqueous composition, in an electric fragrance diffuser operating with a piezoelectric ceramic, characterised in that said scented aqueous composition comprises 0.1% to 0.3% by weight with respect to the total weight of said composition of a fragrance of an essential oil and/or of raw materials of natural or synthetic fragrance, 0.1 to 1% by weight with respect to the total weight of said composition of a fragrance of a non-ionic surfactant agent, and 0.01 to 0.1% by scented weight with respect to the total weight of said composition of a fragrance of a preserving agent.

7 Claims, No Drawings

USE IN AN ELECTRIC PERFUME DIFFUSER OF AN AQUEOUS PERFUME COMPOSITION CONTAINING A SURFACTANT AND A PRESERVATIVE

CROSS-REFERENCE TO RELATED APPLICATIONS

The present application is a filing under 35 U.S.C. 371 as the National Stage of International Application No. PCT/FR2020/051137, filed Jun. 30, 2020, entitled "USE IN AN ELECTRIC PERFUME DIFFUSER OF AN AQUEOUS PERFUME COMPOSITION CONTAINING A SURFACTANT AND A PRESERVATIVE," which claims priority to French Application No. 1908306 filed with the Intellectual Property Office of France on Jul. 22, 2019, both of which are incorporated herein by reference in their entirety for all purposes.

The present invention generally relates to the use of a scented composition with a surfactant and preserving agent base, in an electric fragrance diffuser operating with a piezoelectric ceramic.

Generally, this type of electric fragrance diffuser is known to those skilled in the art and is already marketed. It is used typically using small vials of essential oils that the consumer purchases separately. The consumer fills the water diffuser, then introduces therein a few drops of essential oils. During operation, a mist is formed and the air is scented. The intensity of the electric diffuser is adjusted by the user with the risk that the user incorporates an excessive amount of essential oil, which can expose the user to a danger or on the contrary that the user is disappointed if the quantity introduced is insufficient.

In order to resolve this difficulty, the Applicant has developed a scented composition in an aqueous solution with an essential oil, and/or raw materials of natural or synthetic fragrance base, that can have in particular aromacological virtues and being directly ready for use. Such a composition is intended to be used as is in an electric fragrance diffuser operating with a piezoelectric ceramic.

With such a composition, it is necessary to use a surfactant, in order to render the essential oil and the aqueous phase miscible and thus form a thermodynamically stable emulsion.

The surfactant is an amphiphilic species i.e. having hydrophilic portions and a lipophilic portion. In the case of an anionic surfactant, the hydrophilic portion is negatively charged, while in the case of a cationic surfactant, the hydrophilic portion is positively charged. If the surfactant is of an amphoteric nature, the hydrophilic portion is positively or negatively charged, in such a way that the global charge of the molecule is zero. In the case of the present invention, the surfactant used in the scented composition is non-ionic, i.e. the surfactant molecule includes no net charge. Non-ionic surfactants have the advantages of being inexpensive, renewable, biodegradable, low toxicity and with a low foaming power. However, as with the other types of surfactants, they have the disadvantage of being difficult to vaporise using the piezoelectric system.

Consequently, in operation, residues on the piezoelectric ceramic are unavoidable and can generate a fouling or a premature deterioration of the ceramic. Furthermore, greasy fallouts onto the base or the counter on which the electric diffuser is placed are also expected, due to the foaming properties of surfactants, during the vaporisation of the fragrance.

In order to overcome the aforementioned disadvantages, the applicant has developed a composition of a fragrance intended to be used in an electric diffuser operating with a piezoelectric ceramic. The choice of the surfactant and the percentage thereof must be adapted to limit the disadvantages described hereinabove while still guaranteeing the performance sought: Olfactory quality, olfactory intensity and aromacological promise.

More particularly, the present invention has for object the use of a scented aqueous composition, in an electric fragrance diffuser operating with a piezoelectric ceramic, characterised in that said scented aqueous composition comprises 0.1% to 0.3% by weight with respect to the total weight of said composition of a fragrance of an essential oil and/or of raw materials of natural or synthetic fragrance, 0.1 to 1% by weight with respect to the total weight of said composition of a fragrance of a non-ionic surfactant agent, and 0.01 to 0.1% by weight with respect to the total weight of said composition of a fragrance of a preserving agent.

By using such a scented composition, the consumer does not need to adjust the intensity of the fragrance that the electric diffuser has to diffuse Advantageously, it is possible to use, in the framework of the present invention, a polysorbate as a surfactant, and preferably polyoxyethylene 20 sorbitan monolaurate.

Advantageously, it is possible to use, in the framework of the present invention, as a preserving agent, a biocide, and preferably 1,2-benzisothiazlin-3-one in a 20% aqueous solution, present at a rate of 0.1% by weight with respect to the total weight of said composition of a fragrance.

Other advantages and particularities of the present invention will result from the following examples given as non-limiting examples.

EXAMPLES

Products
  scented formulations marketed by PRODUITS BERGER for the "electric diffuser" range under the trade names: "Pomme vanille", "Paris Chic", and "Caresse de coton";
  Surfactant: polyoxyethylene 20 sorbitan monolaurate, marketed under the trade name Tween 20;
  Preserving agent: 1,2-benzisothiazlin-3-one in a 20% aqueous solution, present at a rate of 0.1% by weight.
Tests
  The olfactory quality of the various formulations used in an electric piezoelectric ceramic diffuser is evaluated olfactively in an actual situation in a room, as well as the residual percentage of residues on the ceramic after 5 to 7 hours of operation of the diffuser.

The results of the tests are indicated hereinafter, in table 1:

TABLE 1

| Formulation | % of fragrance | % of tween 20 Solution tested | Olfactory quality |
|---|---|---|---|
| Pomme Vanillé UC | 0.1 | 0.6 | OK |
| Paric Chic | 0.1 | 0.3 | OK |
| Caresse de coton | 0.1 | 0.2 | OK |

The percentage of the residue of the formula on the ceramic is less than 1% with respect to the total weight of the formula before use.

The invention claimed is:

1. A method comprising:
   releasing a scented aqueous composition, in an electric fragrance diffuser operating with a piezoelectric ceramic, characterised in that said scented aqueous composition comprises 0.1% to 0.3% by weight with respect to the total weight of said composition of a fragrance of an essential oil and/or of raw materials of natural or synthetic fragrance, 0.1 to 1% by weight with respect to the total weight of said composition of a fragrance of a polysorbate, and 0.01 to 0.1% by weight with respect to the total weight of said composition of a fragrance of a preserving agent.

2. The method according to claim 1, according to which the preserving agent is a biocide.

3. The method according to claim 2, wherein the biocide is 1,2-benzisothiazlin-3-one.

4. The method according to claim 3, wherein the biocide is in a 20% aqueous solution.

5. The method according to claim 2, wherein the biocide is present at a rate of 0.1% by weight with respect to the total weight of said composition of a fragrance.

6. The method according to claim 1, wherein the polysorbate is polyoxyethylene 20 sorbitan monolaurate.

7. A method comprising:
   releasing a scented aqueous composition, in an electric fragrance diffuser operating with a piezoelectric ceramic, characterised in that said scented aqueous composition comprises 0.1% to 0.3% by weight with respect to the total weight of said composition of a fragrance of an essential oil and/or of raw materials of natural or synthetic fragrance, 0.1 to 1% by weight with respect to the total weight of said composition of a fragrance of a non-ionic surfactant agent, and 0.01 to 0.1% by weight with respect to the total weight of said composition of a fragrance of a biocide consisting essentially of 1,2-benzisothiazlin-3-one.

* * * * *